United States Patent [19]

Hedglin et al.

[11] Patent Number: 4,634,691

[45] Date of Patent: Jan. 6, 1987

[54] METHOD FOR INHIBITING TUMOR METASTASIS

[75] Inventors: Walter L. Hedglin, Fairfield; Raymond R. Martodam, Cincinnati, both of Ohio

[73] Assignee: The Procter & Gamble Company, Cincinnati, Ohio

[21] Appl. No.: 459,164

[22] Filed: Jan. 19, 1983

Related U.S. Application Data

[63] Continuation of Ser. No. 297,462, Aug. 28, 1981, abandoned, which is a continuation-in-part of Ser. No. 194,750, Oct. 7, 1980, abandoned.

[51] Int. Cl.⁴ ............................................. A61K 31/66
[52] U.S. Cl. .................................................... 514/108
[58] Field of Search ......................... 424/204; 514/108

[56] References Cited

U.S. PATENT DOCUMENTS

| | | | |
|---|---|---|---|
| 3,553,314 | 1/1971 | Francis | 424/49 |
| 3,553,315 | 1/1971 | Francis | 424/49 |
| 3,584,124 | 6/1971 | Francis | 424/204 |
| 3,584,125 | 6/1971 | Francis | 424/204 |
| 3,641,246 | 2/1972 | Francis | 424/204 |
| 3,662,066 | 5/1972 | Francis | 424/204 |
| 3,678,164 | 7/1972 | Francis | 424/204 |
| 3,683,080 | 8/1972 | Francis | 424/204 |
| 3,965,254 | 6/1976 | Francis et al. | 424/1 |

OTHER PUBLICATIONS

Von Bruekelen, et al., *Lancet* 1:803–805 (1979).
Siris, et al., *N. Engl. J. Med.* 302(6):310–315 (1980).
Orr, et al., *Science* 203:176–179 (1979).

*Primary Examiner*—Jerome D. Goldberg
*Attorney, Agent, or Firm*—Steven J. Goldstein; Jack D. Schaeffer; Richard C. Witte

[57] ABSTRACT

A method for inhibiting the formation of tumor cell metastases without treating the underlying cancer itself in humans and animals having metastatic cancer involving the skeleton is disclosed. In this method of treatment, a safe and effective amount of ethane-1-hydroxy-1,1-diphosphonic acid, dichloromethane diphosphonic acid or a pharmaceutically-acceptable salt or ester, such as the sodium salt, of these acids is administered.

8 Claims, No Drawings

METHOD FOR INHIBITING TUMOR METASTASIS

TECHNICAL FIELD

This is a continuation of application Ser. No. 297,462, filed Aug. 28, 1981, now abandoned, which is a continuation-in-part of copending U.S. patent application, Ser. No. 194,750, filed Oct. 7, 1980 now abandoned.

The present invention provides a method for inhibiting the formation of tumor cell metastases without treating the underlying cancer itself in humans and animals afflicted with metastatic cancer involving the skeleton.

The spread of cancer cells from a primary tumor site to distant organs is known as metastasis. Metastasis has been considered one of the most intriguing aspects of the pathogenesis of cancer. This is certainly true to the extent that cancer tumor metastasis is responsible for most therapeutic failures in treating the disease, as patients succumb to the multiple tumor growth. See, for example, Cancer, A Comprehensive Treatise, F. F. Becker (editor), Volume 4, Chapter 3, Plenum Press, New York, 1975.

Bone is one of the more common sites in the body for metastasis of tumore cells, i.e., bone is a prime site for the formation of secondary tumors. Indeed, certain types of cancer, such as breast cancer, lung cancer, and prostate cancer, are characterized by an especially high rate of bone metastases. Thus, the discovery of a safe and effective agent, used as one component in a treatment regimen for metastatic cancers, for inhibiting the formation of tumor cell metastases to bone would constitute a significant medical development.

BACKGROUND ART

Various diphosphonate materials, including dichloromethane diphosphonic acid and ethane-1-hydroxy-1,1-diphosphonic acid and their salts and esters, are known to be effective in inhibiting deposition and mobilization of calcium phosphate in the body. As a result, these compounds are useful in the treatment and prevention of pathological calcification and hard tissue demineralization conditions. See, U.S. Pat. No. 3,683,080, Francis, issued Aug. 8, 1972. Radio-tagged diphosphonates, especially ethane-1-hydroxy-1,1-diphosphonic acid and dichloromethane diphosphonic acid, have been taught to be effective in the treatment of calcific tumors. U.S. Pat. No. 3,965,254, Francis, issued June 22, 1976. When used in this way, the diphosphonate group locates the molecule at the site of the calcific tumor, while the treatment is provided by the radioisotope portion. There has also been a suggestion that (3-amino-1-hydroxypropylidene)-1,1-bisphosphonate, a substance which can cause significant undesirable side effects, may act to inhibit tumor-induced osteolysis when administered to breast cancer patients having hypercalcemia. S. J. M. Von Bruekelen, et al., Inhibition of Osteolytic Bone Lesions by APD, Lancet, Volume 1, pages 803–805 (Apr. 14, 1979). However, there has been no suggestion in the art that any of these organophosphonates is useful in minimizing tumor cell metastasis to bone, i.e., that these compounds represent a therapeutic alternative for use early in the development of the cancer to minimize the spread of cancer cells from a primary tumor site to the skeleton.

Orr, et al., concluded, in a study utilizing rat mammary tumor cells, that a factor(s) which is chemotactic for tumor cells is produced by bone and is released when the bone is resorbed. These data led to the hypothesis that the release of this chemotactic factor(s) causes tumor cells which have migrated from the main tumor site to become attracted and attached to bone, beginning the formation of a new metastasized tumor. See William Orr, et al., Chemotatic Responses of Tumor Cells to Products of Absorbing Bone, Science, 203, 176–179 (1979).

It has now been found that the use of ethane-1-hydroxy-1,1-diphosphonic acid, dichloromethane diphosphonic acid or their pharmaceutically-acceptable salts and esters, compounds which are known to be safely administered to humans and animals, significantly reduces the incidence of tumor cell metastasis to bone.

It is, therefore, an object of the present invention to provide a safe and effective method for inhibiting the formation of tumor cell metastases without teating the underlying cancer itself in humans and animals having metastatic cancer involving the skeleton.

SUMMARY OF THE INVENTION

The present invention relates to a method for inhibiting the formation of tumor metastases without treating the underlying cancer itself in humans or animals comprising the administration of a safe and effective amount of a compound selected from the group consisting of ethane-1-hydroxy-1,1-diphosphonic acid, dichloromethane diphosphonic acid and pharmaceutically-acceptable salts and esters thereof to a patient having metastatic cancer involving the skeleton.

DETAILED DESCRIPTION OF THE INVENTION

The treatment regimens encompassed by the present invention employ a safe and effective amount of a pharmaceutically-acceptable ethane-1-hydroxy-1,1-diphosphonate or dichloromethane diphosphonate compound. These compounds are administered to inhibit the metastasis to bone sites in humans and animals of cancer tumor cells. The dichloromethane diphosphonates utilized herein are conveniently abbreviated as "Cl$_2$MDP"; the ethane-1-hydroxy-1,1-diphosphonates utilized herein are abbreviated "EHDP".

The phrase "safe and effective amount of EHDP or Cl$_2$MDP compound", herein, means sufficient EHDP or Cl$_2$MDP compound to desirably affect and inhibit the metastasis of tumor cells, at a reasonable benefit/risk ratio attendant with any medical treatment. Within the scope of sound medical judgment, the required dosage of EHDP or Cl$_2$MDP will vary with the severity of the condition being treated, the duration of the treatment, the nature of adjunct treatment, the age and physical condition of the patient, the specific diphosphonate compound employed, and like considerations discussed more fully hereinafter.

"Pharmaceutically-acceptable", as used herein, means that the EHDP or Cl$_2$MDP compound and other ingredients used in the compositions employed herein are suitable for use in contact with the tissues of humans and lower animals without undue toxicity, irritation, allergic response, and the like, commensurate with a reasonable benefit/risk ratio.

The term "administration" of the EHDP or Cl$_2$MDP compounds and compositions, as used herein, includes systemic use, as by injection (especially parenterally), intravenous infusion, suppositories and oral administration thereof, as well as topical application of the compounds and compositions.

The term "comprising", as used herein, means that various other compatible drugs and medicaments, as well as inert ingredients, can be conjointly employed in the therapeutic methods of this invention, as long as the critical EHDP and Cl₂MDP compounds are used in the manner disclosed. The term "comprising" thus encompasses and includes the more restrictive terms "consisting of" and "consisting essentially of".

By "compatible" herein is meant that the components of the compositions used in the practice of this invention are capable of being commingled without interacting in a manner which would substantially decrease the efficacy of the EHDP or Cl₂MDP compositions under ordinary use situations.

All percentages and ratios used herein are by weight, unless otherwise specified.

The Cl₂MDP compounds used in the practice of this invention have the formula

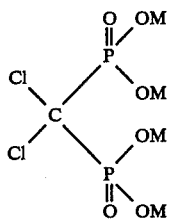

where M is hydrogen, a pharmaceutically-acceptable cation (such as, an alkali metal, especially sodium or potassium), or an alkyl or aryl moiety (such as methyl, ethyl, propyl, butyl, phenyl, or the like).

The EHDP compounds useful herein have the formula

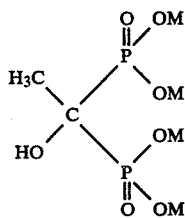

wherein M is as defined above. Preferred EHDP salts include the trisodium hydrogen salt and the disodium dihydrogen salt. Mixtures of EHDP and Cl₂MDP are also useful herein.

The dichloromethane diphosphonates used herein can be prepared in the manner described in Organic Phosphorous Compounds, Volume 7, Kosolapoff and Maier (1976), page 258 (citing references). In general, the reaction sequence for the preparation of Cl₂MDP compounds involves an Arbuzov-type rearrangement of dibromomethane with triisopropyl phosphite, followed by chlorination and acidulation to prepare the Cl₂MDP, free acid form. The acid form can be neutralized with any desired (pharmaceutically-acceptable) base or can be esterified, to provide additional Cl₂MDP compounds for use in the present invention. The EHDP compounds can be prepared using the procedure described in U.S. Pat. No. 3,400,149, Quimby, et al., issued Sept. 3, 1968, incorporated herein by reference.

The following experiments demonstrate the heretofore unsuspected ability of the compositions of the present invention to desirably inhibit the metastasis of tumor cells to bone.

Bone-conditioned media were obtained from fetal long bone cultures as described by Raisz, L. G., *J. Clin. Invest.* 44, 103-116 (1965). On the 18th day of gestation, pregnant Sprague Dawley (Charles River) rats were injected with 200 $\mu$Ci$^{45}$Ca. On the following day, the rats were sacrificed and the fetal radii and ulnae explanted for organ culture. After 24 hours, the culture media were replaced with fresh culture media, culture media containing parathyroid hormone (PTH) (a stimulator of bone resorption) or PTH and Cl₂MDP. After five days, aliquots of the media were taken to determine the $^{45}$Ca in culture and, when compared with the calcium in the bones, used to calculate percent bone resorption. As can be seen from the following tables, PTH induced bone resorption and Cl₂MDP inhibited this bone resorption. These media were then tested for their ability to support Walker 256 tumor cell chemotaxis in Boyden chambers as described by Orr, et al., *Science* 203, 176-179 (1979). Bone culture media in the bottom chamber were separated from the tumor cells in the top chamber by a 12 micron nitrocellulose filter. After a 4-hour incubation in 5% CO₂ at 37° C. the filters were removed from the chambers and stained with hematoxylin. Chemotaxis was measured by counting the number of cells that migrated 10 microns or further into the filter. As can be seen, during two different experiments PTH stimulated bone resorption and this medium supported significantly more chemotaxis than did the control medium. Cl₂MDP at 10 $\mu$g/ml completely inhibited PTH-stimulated bone resorption and this medium was no more chemotactic than control media. These experiments indicated that Cl₂MDP is capable of inhibiting tumor cell chemotaxis to products of resorbing bone.

| Treatment | % Bone Resorption | No. Cells that Chemotaxed |
|---|---|---|
| Experiment I | | |
| (1) Control media | — | 16 ± 3 |
| (2) Control bones | 20 | 12 ± 3 |
| (3) Bones + .5 u/ml PTH | 76 | 25 ± 4 |
| (4) Bones + .5 u/ml PTH and 10 $\mu$g/ml Cl₂MDP | 19 | 14 ± 5 |
| (5) Trypsinized C₅A* | — | 30 ± 2 |
| Experiment II | | |
| (1) Control media | — | 7 ± 3 |
| (2) Control bones | 21.7 | 5 ± 1 |
| (3) Bones + .5 u/ml PTH | 67.7 | 16 ± 3 |
| (4) Bones + .5 u/ml PTH and 10 $\mu$g/ml Cl₂MDP | 15.4 | 8 ± 3 |
| (5) Trypsinized C₅A* | — | — |

*C₅A a component of the complement system becomes a chemotactic attractant for Walker 256 tumor cells when trypsinized.

The method of treatment disclosed and claimed herein may be used as a part of the treatment regimen for a patient having a metastatic cancer characterized by skeletal involvement. Breast cancer, prostate cancer, and lung cancer are well-known to have a high incidence of tumor cell metastases to bone. The treatment to inhibit metastases to bone is best administered as early after the detection of the cancer as possible. Hypercalcemia occurs in patients having a relatively high degree of skeletal metastasis. By utilizing the treatment regimen in patients not exhibiting hypercalcemia, the treating physician maximizes the chances that significant skeletal metastasis has not yet occurred; this maximizes chances for successful treatment. In such a regimen, the EHDP or Cl$_2$MDP may, and generally will, be administered together with a form of therapy used for controlling the primary tumor, itself. Examples of such treatments include, but are not limited to, radiation therapy and compatible antitumor drugs (such as Adriamycin). The treatment described in the present application may also be used conjointly with (i.e., either preceding or subsequent to) a surgical procedure to remove the primary tumorous material from the body. Frequently surgical procedures to remove tumorous material from the body are avoided because of the fear that the physical manipulation involved will cause metastasis of tumor cells. By administering EHDP or Cl$_2$MDP to the patient prior to the surgical procedure, the risk of metastasis to bone resulting from the surgery can be greatly reduced, making surgery a more appealing treatment option.

Within the scope of sound medical judgment, the dosage of EHDP or Cl$_2$MDP used in the present invention will vary with the severity and nature of the particular condition being treated, the duration of treatment, the adjunct therapy used, the age and physical condition of the patient, and like factors within the specific knowledge and expertise of the attending physician. However, The method of treatment disclosed and claimed herein may be used as a part of the treatment regimen for a patient having a metastatic cancer characterized by skeletal involvement. Breast cancer, prostate cancer, and lung cancer are well-known to have a high incidence of tumor cell metastases to bone. The treatment to inhibit the formation of metastases to bone is best administered as early after the detection of the cancer as possible. Hypercalcemia occurs in patients having a relatively high degree of skeletal metastasis. By utilizing the treatment regimen in patients not exhibiting hypercalcemia, the treating physician maximizes the chances that significant skeletal metastasis has not yet occurred; this maximizes chances for successful treatment. In such a regimen, the EHDP or Cl$_2$MDP may, and generally will, be administered together with a form of therapy used for controlling the primary tumor, itself. Examples of such treatments include, but are not limited to, radiation therapy and compatible antitumor or antineoplastic agents. Examples of such antineoplastic agents include melphalan (available as Alkeran from Borroughs-Wellcome, Ltd.), lomustine capsules (available as Cee Nu from Bristol-Myers Pharmaceutical Group), cyclophosphamide (available as Cytoxan from Bristol-Myers Pharmaceutical Group or Procytox from Frank W. Horner, Inc.), estramustine phosphate disodium capsules (available as Emcyt from Hoffmann-La Roche), ethinyl estradiol tablets USP (available as Estinyl from Schering), fluoxymesterone tablets (available as Halotestin from Upjohn); diethylstilbestrol diphosphate (available as Honvol from Frank W. Horner, Inc.), metotane tablets (available as Lysodren from Bristol-myers Pharmaceutical Group), doxorubicin HCl for injection (available as Adriamycin from Adria Laboratories), fluorourocil (available from Adria Laboratories or from Hoffmann-La Roche), amethopterin (available as Methotrexate from Lederle), and tamoxifen citrate tablets (available as Nolvadex from ICI Pharmaceuticals). The treatment described in the present application may also be used conjointly with (i.e., either preceding or subsequent to) a surgical procedure to remove the primary tumorous material from the body. Frequently surgical procedures to remove tumorous material from the body are avoided because of the fear that the physical manipulation involved will cause metastasis of tumor cells. By administering EHDP or Cl$_2$MDP to the patient prior to the surgical procedure, the risk of metastasis to bone resulting from the surgery can be greatly reduced, making surgery a more appealing treatment option.

Within the scope of sound medical judgement, the dosage of EHDP or Cl$_2$MDP used in the present invention will vary with the severity and nature of the particular condition being treated, the duration of treatment, the adjunct therapy used, the age and physical condition of the patient, and like factors within the specific knowledge and expertise of the attending physician. However, single dosages can typically range from 0.01 to 500 milligrams per kilogram of body weight, preferably 0.5 to 50 milligrams per kilogram (unless otherwise specified, the unit designated "mg/kg", as used herein, refers to milligrams per kilogram of body weight). The higher dosages within this range are usually required in the case of oral administration because of the somewhat limited absorption of EHDP and Cl$_2$MDP through the gut. Up to four doses per day can be used routinely, but this can be varied according to the needs of the patient, consistent with a sound benefit/risk ratio. Dosages greater than about 500 mg/kg may produce untoward symptoms and are usually avoided; moreover, daily dosages greater than about 2000 mg/kg are not ordinarily required to produce the desired benefit and may produce toxic side effects. Again, however, patient to patient variation in response may be expected. Dosages as low as about 0.01 mg/kg/day are useful, especially if administered intravenously. Preferred daily dosages range from about 1 mg/kg to about 200 mg/kg.

Preferably, dosages ranging from about 10 to about 100 mg/kg are employed when the diphosphonate is administered orally.

For parenteral administration (S.C., I.P., I.M.), diphosphonate dosages are preferably from about 0.5 mg/kg/day to about 20 mg/kg/day. For long term parenteral infusion (I.V.) the most highly preferred dosage range is from about 1 mg/kg/day to about 5 mg/kg/day.

For purposes of oral administration the EHDP or Cl$_2$MDP can be formulated in the form of capsules, tablets or granules. For treatment of non-human animals, the diphosphonate is preferably incorporated in animal feed, feed supplements or feed concentrates. EHDP or Cl$_2$MDP can also be prepared in unit dosage form together with a pharmaceutical carrier, each unit dosage form containing from about 15 mg to 10 g of active material. The preferred concentration range of diphosphonate in unit dosage forms intended for use by humans and smaller domesticated animals is from 15 mg to 1000 mg, more preferably 100 mg to 500 mg. A higher concentration range, i.e., from 1 gram to 5 grams is preferred in unit dosage forms intended for treatment of larger animals, such as cows or horses.

As used herein, the term "pharmaceutical carrier" denotes a solid or liquid filler, diluent or encapsulating substance. Some examples of the substances which can serve as pharmaceutical carriers are sugars, such as lactose, glucose and sucrose; starches, such as corn starch and potato starch; cellulose and its derivatives, such as sodium carboxymethyl cellulose, ethyl cellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; agar; alginic acid; pyrogen-free water; isotonic saline; and phosphate buffer solutions, as well as non-toxic compatible substances used in pharmaceutical formulations. Wetting agents and lubricants, such as sodium lauryl sulfate, as well as coloring agents, flavoring agents, tableting agents, and preservatives, can also be present. Tableting is done using conventional techniques.

The pharmaceutical carrier employed in conjunction with the EHDP or Cl$_2$MDP is used at a concentration sufficient to provide a practical size to dosage relationship. Preferably, the pharmaceutical carrier comprises from about 0.1% to 99% by weight of the total composition.

The following examples illustrate compositions and methods used in the practice of this invention, but are not intended to be limiting thereof.

EXAMPLE I

Gelatin capsules are prepared by conventional methods, as follows:

| Ingredients | Milligrams per Capsule |
| --- | --- |
| Cl$_2$MDP (Mixture of di- and trisodium salt) | 350.0 |
| Starch | 50.0 |

The above capsule when administered twice daily to a patient having a metastatic cancer involving the skeleton (such as breast, lung or prostate cancer) acts to inhibit the mestastasis of the tumor cells to bone. These capsules are also beneficially used conjointly with known anti-tumor drugs, such as Adriamycin.

The sodium salt form of Cl$_2$MDP is preferred for use herein. However, the potassium salt form of Cl$_2$MDP and the C$_1$–C$_4$ alkyl esters of Cl$_2$MDP can be substituted for the Cl$_2$MDP, sodium salts, in the composition of Example I with similar results. The Cl$_2$MDP component in Example I may also be replaced, in whole or in part, with EHDP (preferably a mixture of di- and trisodium salts) and similar results are obtained.

EXAMPLE II

Tablets are prepared by conventional methods, formulated as follows:

| Ingredient | Milligrams per Tablet |
| --- | --- |
| EHDP (trisodium hydrogen salt) | 250.0 |
| Lactose | 40.0 |
| Starch | 2.5 |
| Magnesium stearate | 1.0 |

The above composition is administered 4 times daily to a patient having breast cancer and weighing approximately 70 kilograms, to inhibit the metastasis to bone of the breast cancer tumor cells. Similar results are obtained when Cl$_2$MDP (disodium salt) replaces the EHDP in the above composition, in whole or in part.

EXAMPLE III

Solutions for parenteral administration or topical administration are prepared by dissolving Cl$_2$MDP (acid form) in water at concentrations of about 1% to 10%, adjusting the pH to about 7.4 with a pharmaceutically-acceptable base corresponding to the desired salt form, and sterilizing the resulting solution by standard sterilization techniques.

The Cl$_2$MDP solutions prepared in the foregoing manner can be administered parenterally by subcutaneous, intradermal, intramuscular or intravenous injection, or I.V. infusion. The usual, and preferred dosage ranges for these modes of administration are as follows:
subcutaneous 0.05 to 10 mg/kg
intradermal 0.05 to 10 mg/kg
intramuscular 0.05 to 5 mg/kg
intravenous 0.05 to 5 mg/kg

What is claimed is:

1. A method for inhibiting the formation of new tumor metastases without treating the underlying cancer itself in humans or animals comprising administering an amount, which is safe and sufficient to inhibit the formation of tumor metastases, of a compound selected from the group consisting of ethane-1-hydroxy-1,1-diphosphonic acid, dichloromethane diphosphonic acid and pharmaceutically-acceptable salts thereof to a patient having breast cancer, lung cancer or prostate cancer.

2. The method according to claim 1 wherein the daily dosage of compound administered is from about 0.01 to about 2,000 mg/kg body weight.

3. The method according to claim 2 wherein the daily dosage administered is from about 1 to about 200 mg/kg body weight.

4. The method according to claim 3 wherein the compound administered is a sodium salt form of dichloromethane diphosphonic acid.

5. The method according to claim 3 wherein the compound administered is a sodium salt form of ethane-1-hydroxy-1,1-diphosphonic acid.

6. The method according to claim 2 carried out in preparation for a surgical procedure to remove tumorous material.

7. The method according to claim 2 wherein the compound is administered promptly after the detection of the cancer.

8. The method according to claim 2 wherein the human or animal being treated does not exhibit hypercalcemia.

* * * * *